US00PP30634P2

(12) United States Plant Patent
van Zoest

(10) Patent No.: US PP30,634 P2
(45) Date of Patent: Jul. 2, 2019

(54) ***CLEMATIS* PLANT NAMED 'ZO09146'**

(50) Latin Name: ***Clematis* hybrid**
Varietal Denomination: Zo09146

(71) Applicant: Jan van Zoest, Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 15/932,681

(22) Filed: Apr. 5, 2018

(30) Foreign Application Priority Data

Feb. 8, 2018 (EM) ..... 20180436

(51) Int. Cl.
*A01H 5/02* (2018.01)

(52) U.S. Cl.
USPC ..... Plt./228

(58) Field of Classification Search
USPC ..... Plt./228
See application file for complete search history.

*Primary Examiner* — Annette H Para
(74) *Attorney, Agent, or Firm* — Penny J. Aguirre

(57) ABSTRACT

A new cultivar of hybrid *Clematis*, 'Zo09146', that is characterized by its nearly upright and slightly nodding facing flowers, its flowers that are pale purple in color that retain their color with very little or no fading, its good vase life as a cut flower, and its sterility and no seed is produced.

2 Drawing Sheets

Botanical classification: *Clematis* hybrid.
Variety denomination: 'Zo09146'.

BACKGROUND OF THE INVENTION

The present invention relates to a new and distinct cultivar of *Clematis* of hybrid origin (Diversifolia Group) and will be referred to hereafter by its cultivar name 'Zo09146'. *Clematis* 'Zo09146' is a deciduous plant grown for use as a cut flower.

*Clematis* 'Zo09146' was derived from an ongoing breeding program by the Inventor at his nursery in Boskoop, The Netherlands. The goal of the selection was to select a new cultivar of *Clematis* with pink flowers to be used as a cut flower. 'Zo09146' was selected in 2009 and arose from a controlled cross made in 2007 between unnamed and unpatented plants from his breeding program; the female parent designated as No. 19960065 and the male parent designated as No. 20020159.

Asexual propagation of the new cultivar was first accomplished by internodial stem cuttings under the direction of the Inventor in Boskoop, The Netherlands in 2009. Asexual propagation by internodial stem cutting has determined that the characteristics of the new cultivar are stable and are reproduced true to type in successive generations.

SUMMARY OF THE INVENTION

The following traits have been repeatedly observed and represent the characteristics of the new cultivar as grown outdoors and observed for four years in Boskoop, The Netherlands. These attributes in combination distinguish *Clematis* 'Zo09146' as a unique cultivar of *Clematis*.

1. 'Zo09146' exhibits nearly upright and slightly nodding facing flowers.
2. 'Zo09146' exhibits flowers that are pale purple in color.
3. 'Zo09146' exhibits flowers that retain their color with very little or no fading.

4. 'Zo09146' exhibits good vase life as a cut flower.
5. 'Zo09146' is sterile and no seed is produced.

'Zo09146' differs from its female parent in having flowers that are almost upright and spreading while the female parent has nodding bell-shaped flowers. 'Zo09146' differs from its male parent in having smaller, slightly nodding flowers with primarily 6 tepals (sometimes 5) while the male parent has larger and upright flowers with 6 to 8 tepals.

'Zo09146' can be most closely compared to the cultivars *Clematis* 'Hagley Hybrid' (not patented) and *Clematis* 'Margaret Hunt' (not patented), differences are described in TABLE 1.

TABLE 1

| Clematis cultivar | Characteristic | Description | 'Zo09146' |
|---|---|---|---|
| 'Hagley Hybrid' | Stigma color | cream | pale purple |
| 'Hagley Hybrid' | Style length | as long as the inner stamens | just slightly longer then inner stamens |
| 'Hagley Hybrid' | Plant habit | woody | herbaceous |
| 'Hagley Hybrid' | Filament color | pale purple | pale yellow |
| 'Margaret Hunt' | Stigma color | cream | pale purple |
| 'Margaret Hunt' | Style length | distinctly longer then inner stamens | just slightly longer then inner stamens |
| 'Margaret Hunt' | Habit | climber | perennial |
| 'Margaret Hunt' | Filament color | white | pale yellow |

BRIEF DESCRIPTION OF THE DRAWINGS

The accompanying colored photographs illustrate the overall appearance and distinct characteristics of the new *Clematis*. The photographs were taken of cut flower branches taken from a two-year-old plant as grown outdoors in Tanzania.

The photograph in FIG. 1 provides a close-up view of a bouquet of flowers.

Figure 1:
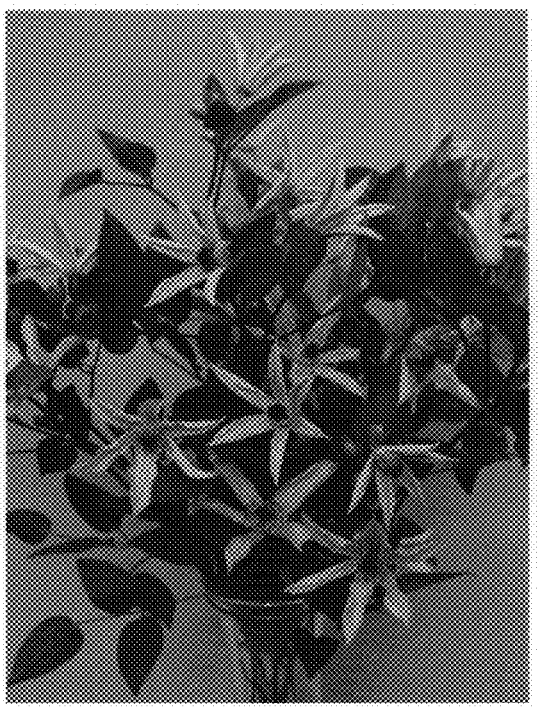
Figure 2:
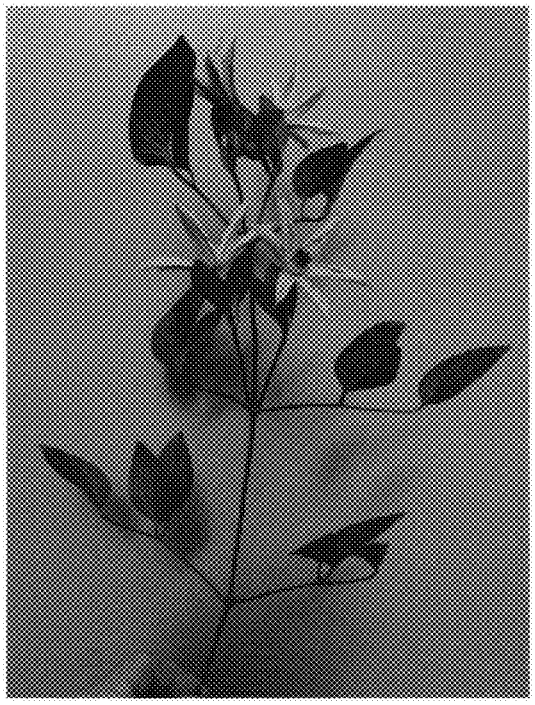

The photograph in FIG. 2 provides a view of a cut flower branch.

Figure 3:
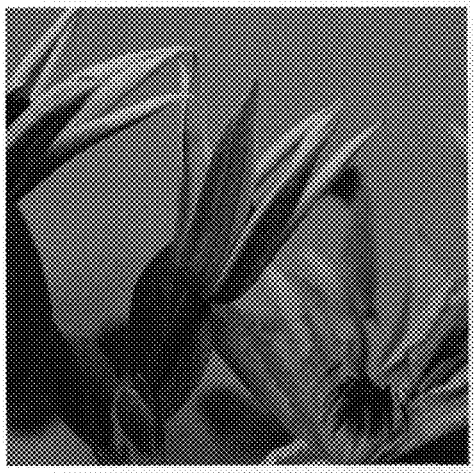

The photograph in FIG. 3 provides a close-up view of an opening flower bud.

Figure 4:
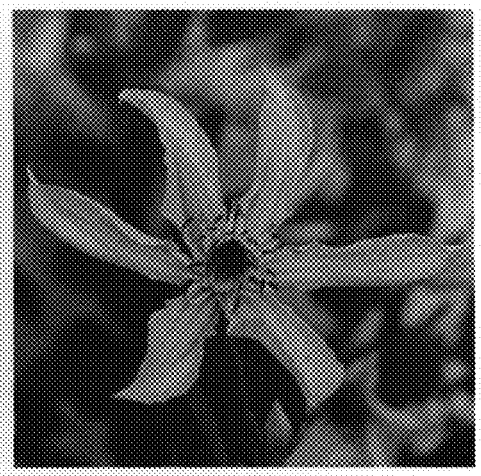

The photograph in FIG. 4 provides a close-up view of fully open flower.

Figure 5:
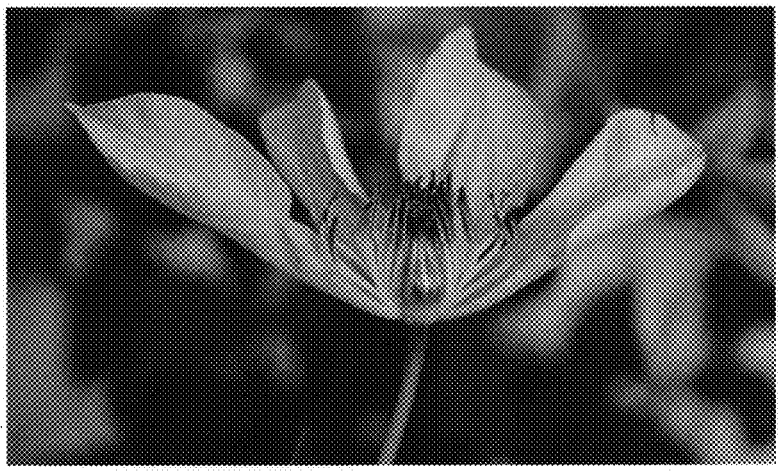

The photograph in FIG. 5 provides a view of a flower with 2 tepals removed to provide a close up of the stamens and pistils.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of three-year-old plants of 'Zo09146' as grown outdoors in full sun at a cut flower nursery in Tanzania. The phenotype of the new cultivar may vary with variations in environmental, climatic and cultural conditions, as the cultivar has not been tested under all possible environmental conditions. The color determination is in accordance with The 2001 Colour Chart of The Royal Horticultural Society, London, England, except where general color terms of ordinary dictionary significance are used.

General description:

*Botanical classification.*—*Clematis* 'Zo09146' (classified in the Diversifolia Group).

*Blooming period.*—Year-round for cut flower production.

*Plant habit.*—Herbaceous perennial.

*Height and spread.*—Three-year-old plant is about 20 cm in width at the base and 90 cm in height when pruned for cut flower production.

*Cold hardiness.*—At least to U.S.D.A. Zone 5.

*Culture.*—Moist but well-drained soils in full sun with the roots shaded.

*Diseases and pests.*—Susceptibility to powdery mildew caused by *Erysiphe polygoni* is unknown, no pest problems have been observed.

*Root description.*—Fleshy.

Growth and propagation:

*Propagation.*—Internodial soft wood cuttings from vegetative shoots.

*Root initiation.*—Roots develop in 5 weeks in summer under greenhouse conditions.

*Time required for root development.*—75 to 90 days to fully develop in a 7-cm container from a 5-cm cutting.

*Growth rate.*—Vigorous and very free flowering for cut flower production.

Stem description:

*Shape.*—Round with 6 angles.

*Stem color.*—175A.

*Stem size.*—Up to 90 cm in length for cut flower production, an average of 3 mm in width.

*Stem surface.*—Sparsely short hairy.

*Internode length.*—6 to 11 cm.

*Branching.*—From the base.

Foliage description:

*Leaf arrangement.*—Opposite.

*Leaf division.*—Ternate.

*Leaf size.*—Up to 15 cm in length and 14 cm in width (including the petiole).

*Leaf attachment.*—Petiolate.

*Leaflet shape.*—Ovate.

*Leaflet base.*—Terminal leaflet obtuse, side leaflets oblique.

*Leaf apex.*—Acuminate.

*Leaf fragrance.*—Just a slight fragrance when crushed.

*Leaf venation.*—Upper surface slightly reticulate, lower surface reticulate, color similar to leaf color on upper and lower surface.

*Leaf margin.*—Entire.

*Leaf surface.*—Upper surface; a few sparse hairs with more densely on the main veins, lower surface; sparsely hairy.

*Leaf color.*—Upper surface; 137A, lower surface; 137C.

*Petioles.*—3 to 5 cm in length, 1 mm in diameter, 134C in color and can be suffused with 178A, shape round but canaliculate on upper surface, surface sparsely hairy.

*Petiolules.*—Terminal leaflet 3 to 5 cm long, side leaflets 0.5 to 1 cm in length, surface sparsely hairy, 134C in color and can be suffused with 178A.

Inflorescence description:

*Inflorescence type.*—Solitary or a 3-flowered dichasial cyme.

*Inflorescence arrangement.*—Terminal and axillary on young shoots.

*Peduncles.*—4 to 6 cm in length, 143C in color, round in shape, surface slightly 6 ribbed and hairy.

*Pedicels.*—4 to 6 cm in length, 143C in color, round in shape, surface slightly ribbed and hairy with hairs denser near the flower.

*Flower buds.*—More or less upright, oblong in shape, apex acuminate, base obtuse, 65C in color with 141D at the base, surface sparsely hairy with villous seams.

*Flower fragrance.*—Slightly sweet.

*Lastingness of the flowers.*—Individual flowers last 7 to 14 days until the first tepal drops, followed later by the stamens depending on the condition when sold as a cut flower.

*Flower quantity.*—4 or 6 flowers per stem when grown for cut production.

*Flower type.*—Almost spreading.

*Flower aspect.*—More or less upright.

*Flower size.*—5 to 9 cm in diameter and 2 cm in depth.

*Flower sex.*—Bisexual.

*Tepal number.*—Typically 6, sometimes 5.

*Tepal shape.*—Lanceolate.

*Tepal apex.*—Acute.

*Tepal base.*—Cuneate.

*Tepal margin.*—Entire.

*Tepal surface.*—Inner surface; glabrous, outer surface; center sparsely hairy and more densely hairy at apex, margin villous.

*Tepal color.*—Inner surface; N82C in the center with 149C at the base, margin N82D, outer surface; center 77D with ribs 77C and at very base 141D, margin 76B.

*Tepal size.*—Up to 4.5 cm in length and an average of 2 cm in width.

*Tepal appearance.*—When opening the tepals remain canaliculate for a long time but will fully spread when the flower gets older.

Reproductive organs:

*Gynoecium*.—Average of 40 to 50 pistils, up to 1.2 cm in length, ovary 145B in color and silvery hairy, style plumose and 159D in color, stigma 79B in color, slightly bend and glabrous.

*Androecium*.—Filaments are 0.3 to 1 cm in length, 0.1 cm in width and linear in shape, surface is glabrous, color 4D at the base to 4C below the anthers; anthers are 0.5 cm in length, 0.5 mm in width, linear in shape, and N81C in color, pollen is 84D in color, connective is 0.5 mm in length, elongated, apex obtuse, surface glabrous and N77D in color.

*Seed*.—Seed is not formed, observed to be sterile.

It is claimed:

1. A new and distinct cultivar of *Clematis* plant named 'Zo09146' as herein illustrated and described.

* * * * *